United States Patent [19]

Weisenfeld

[11] Patent Number: 4,954,466

[45] Date of Patent: Sep. 4, 1990

[54] RECOVERY OF COBALT CATALYST VALUES

[75] Inventor: Robert B. Weisenfeld, Manchester, Mo.

[73] Assignee: Monsanto Company, St. Louis, Mo.

[21] Appl. No.: 443,281

[22] Filed: Nov. 30, 1989

[51] Int. Cl.$^5$ .................. B11J 31/40; B01J 38/68; C10G 51/04; C10G 51/06

[52] U.S. Cl. .................... 502/24; 423/139; 423/140; 423/143; 502/26; 502/27; 562/518

[58] Field of Search ............... 502/24, 26, 27; 423/139, 140, 143; 562/518

[56] References Cited

U.S. PATENT DOCUMENTS

| | | | |
|---|---|---|---|
| 3,766,266 | 10/1973 | Wakamatsu et al. | 562/518 |
| 4,175,109 | 11/1979 | Kim | 423/54 |
| 4,432,949 | 2/1984 | Hubred | 423/139 |
| 4,533,500 | 8/1985 | Chauvin e al. | 260/404 |
| 4,567,284 | 1/1986 | Monzyk et al. | 556/37 |
| 4,882,131 | 11/1989 | Powers et al. | 423/54 |

Primary Examiner—Paul E. Konopka
Attorney, Agent, or Firm—Frank D. Shearin

[57] ABSTRACT

A process is provided for recovering cobalt values from a cobalt-N-acetyliminodiacetic acid complex by dissolving the complex in an aqueous solution of a strong acidic solution, extracting the acid solution with a hydrocarbon solvent containing a trialkylamine to transfer the cobalt from the aqueous solution into the hydrocarbon solvent, stripping the cobalt from the hydrocarbon solvent with water, and precipitating the cobalt from the stripping water by using a strong alkali.

12 Claims, No Drawings

RECOVERY OF COBALT CATALYST VALUES

BACKGROUND OF THE INVENTION

1. Field of the Invention

The present invention relates to the recovery of cobalt catalyst values from a process stream in the manufacture of N-acyliminodiacetic acids. More particularly, the present invention relates to the recovery of cobalt catalyst values from a process stream in the manufacture of N-acyliminodiacetic acids by a process involving ion-pair extraction.

2. Prior Art

U.S. Pat. No. 3,766,266 discloses a process for manufacturing N-acylaminoacids involving reacting an aldehyde with an amide in the presence of carbon monoxide and of a carbonylation catalyst. The patent also discloses that the reactants, i.e., the aldehyde and the amide, can be formed in situ. Suggested catalysts useful in the carbonylation reaction include the transition elements of iron, cobalt and nickel.

U.S. Pat. No. 533,500 discloses that N-acyliminodiacetic acids can be obtained by reacting formaldehyde, or a formaldehyde generator, with an amide, or an amide generator, and with carbon monoxide. The carbonylation catalysts suggested by the prior art include metals of Group VIII of the periodic chart, and more particularly, cobalt. A specifically disclosed cobalt catalyst is dicobaltoctacarbonyl. There is no disclosure in the patent of an effective and economical procedure for recovering the cobalt catalyst at high levels of purity from the reaction product.

U.S. Pat. No. 4,567,284 discloses recovery of a cobalt catalyst by solvent extraction hydrometallurgy. Certain N-alkylalkanohydroxamic acids in a hydrocarbon solvent are suggested to be used to extract the cobalt from an aqueous solution, separating the hydrocarbon solvent cobalt-containing organic phase and recovering the organic phase. While N-alkylalkanohydroxamic acids are known as extractants, they also are known to be chelating agents. The mode of action of hydroxamic chelating agents is to chelate the $Co^{+2}$ ion in order to form an organic soluble species. Such species can be stripped from the organic solution using aqueous ammonia. Unfortunately, when hydroxamic chelating agents are applied to the reaction product of U.S. Pat. No. 533,500, it was found that N-acetyliminodiacetic acid competes effectively as a chelating agent with hydroxamic acid for cobalt ($Co^{+2}$), and thereby renders the use of hydroxamic acids unsatisfactory in recovering cobalt in the presence of N-acetyliminodiacetic acid.

SUMMARY OF THE INVENTION

The present invention provides a process for recovering at high yields cobalt catalyst values from a mixture of cobalt catalyst and N-acetyliminodiacetic acid. The process involves dissolving N-acetyliminodiacetic acid containing a cobalt ($Co^{+2}$) catalyst in a strong mineral acid, such as hydrochloric or hydrobromic acid, preferably concentrated hydrochloric acid. The resulting aqueous solution is contacted with a hydrocarbon solvent comprising at least 5% by weight, preferably about 5-50%, of a quaterizable amine, such as a trialkylamine of the formula

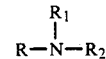

wherein R, $R_1$ and $R_2$ are independently straight or branched chain alkyl radicals having 1-20 or more carbon atoms, preferably 8-16 carbon atoms. The hydrocarbon phase containing the cobalt ($Co^{+2}$) is recovered and stripped with water. The aqueous phase containing the cobalt ($Co^{+2}$) is treated with a base, such as a hydroxide of an alkali metal, such as potassium hydroxide or sodium hydroxide, and/or a carbonate of an alkali metal, such as potassium carbonate or sodium carbonate, or the like. The cobalt precipitates in the form of cobalt hydroxide ($Co(OH)_2$) and/or in the form of cobalt carbonate ($CoCO_3$). The recovery of 90% or more of the cobalt is obtained. In order to reuse the recovered cobalt in the preparation of N-acyliminodiacetic acid, the cobalt carbonate and/or cobalt hydroxide can be simply reacted with a gaseous mixture of carbon monoxide and hydrogen under pressure to regenerate dicobaltoctacarbonyl.

DETAILED DESCRIPTION OF THE INVENTION

Dicobaltoctacarbonyl ($Co_2(CO)_8$) is commonly used to catalyze the reaction of an aldehyde with an amide in the presence of carbon monoxide to produce N-acylaminoacids. N-Acetyliminodiacetic acid is a precursor to iminodiacetic acid and can advantageously be produced using the cobalt catalyzed carbonylation reaction of acetamide, formaldehyde and carbon monoxide. Iminodiacetic acid is produced commercially in large volumes but not by this route to date.

It has been found that when such carbonylation reaction is catalyzed by the presence of cobalt compounds, excellent yields of N-acetyliminodiacetic acid are obtained. Unfortunately, the cobalt is chelated by N-acetyliminodiacetic acid, and the cobalt cannot be conveniently recovered utilizing known techniques, such as solvent extraction using hydroxamic acids as the extractant.

In accordance with the present invention, cobalt ($Co^{+2}$) can be separated from N-acetyliminodiacetic acid by use of a hydrocarbon extractant containing an effective amount of a quaternary forming amine, such as a trialkylamine.

It has been discovered that a class of trialkyl amines can effectively extract cobalt ($Co^{+2}$) from a mixture of the cobalt in the presence of N-acetyliminodiacetic acid. The trialkyl amines may be represented by the following formula

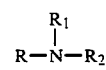

wherein R, $R_1$, and $R_2$ are independently straight or branched chain alkyl radicals having 1-20 or more carbon atoms, preferably 8-16 carbon atoms. The most preferred trialkyl amine is trilauryl amine.

In addition to the above described trialkyl amines, the organic phase of the extractant used in the practice of the present invention comprises a liquid, chemically inert, hydrocarbon solvent. Such solvent must be substantially water immiscible to facilitate separation from aqueous solutions containing N-acetyliminodiacetic acid and the cobalt. Suitable solvents include aliphatic and aromatic hydrocarbons, such as kerosene, hexane, toluene, methylene chloride, chloroform, carbon tetrachloride, xylene, naphtha, cyclohexane, isodecanol, and the like, which perform suitably as an inert solvent in the process of the present invention.

Generally, the trialkyl amine will be present in the liquid hydrocarbon in an amount of at least about 5% by weight. Preferably, the trialkyl amine compound will be present in the amount of 5 to 50%, more preferably about 8–40% by weight based on the total weight of the extractant.

In carrying out the process of this invention, the N-acetyliminodiacetic acid and cobalt chelant complex is dissolved in a strong mineral acid, preferably hydrochloric acid or hydrobromic acid. The amount of acid will be at least sufficient to dissolve the N-acetyliminodiacetic acid-cobalt complex, and to separate the chelant into N-acetyliminodiacetic acid and $Co^{+2}$. When hydrochloric acid is used, the cobalt exists in the aqueous solution as the $CoCl_4^{-2}$ ion. Thus, the reaction of the N-acetyliminodiacetic acid-cobalt chelated complex in aqueous hydrochloric acid may be represented by the following formulas:

$$[Co^{+2}\text{-(N-acetyliminodiacetic acid)}] + 4HCl + 4H_2O \rightleftharpoons CoCl_4^{-2} + 4H_3O^+ + \text{N-acetyliminodiacetic acid} \quad (1)$$

$$(2) \; CoCl_4^{-2} + 6H_2O \rightleftharpoons Co(H_2O)_6^{+2} + 4Cl^- \quad (2)$$

The resulting aqueous solution is extracted with a liquid hydrocarbon solvent containing the trialkyl amine. The extraction involves the selective removal of the amine salt complex of cobalt tetrachloride from the aqueous solution into the organic phase with concomitant expulsion of the smaller counterion ($Cl^-$) into the aqueous phase. The reaction in the extraction and expulsion operations may be represented by the following formulas:

$$(R)_3N + HCl \rightleftharpoons (R)_3NH^+Cl^- \quad (3)$$

$$2(R)_3NH^+Cl^- + CoCl_4^{-2} \rightleftharpoons [(R)_3NH^+]_2CoCl_4^{-2} + 2Cl^- \quad (4)$$

As can be seen from above, after the formation of the $CoCl_4^{-2}$ complex, the cobalt species undergoes an ion exchange reaction with the hydrochloride salt of the trialkylamine. The resulting trialkylamine cationic/cobalt chloride anionic complex is extracted into the organic phase.

After completion of the cobalt extraction step of the process, the organic phase containing the ionic complex is stripped with water, preferably using a plurality of extractions. The aqueous solution from these extractions contains the cobalt in the form of $Co(H_2O)_6^{+2}$. This stripping step may be represented by the following formula:

$$[(R)_3NH^+]_2CoCl_4^{-2} + 6H_2O \rightleftharpoons 2(R)_3N + Co(H_2O)_6^{+2} + 2HCl + 2Cl^- \quad (5)$$

After the aqueous solution containing $Co(H_2O)_6^{+2}$ is removed from the organic phase, the cobalt complex is treated with an aqueous solution of a strong alkali to precipitate the cobalt. The aqueous solution may contain as the strong alkali sodium hydroxide, potassium hydroxide, o the like, which precipitates the cobalt as a water insoluble solid. It is preferred that the treatment with the strong alkali be followed with a treatment with an alkali metal carbonate, such as sodium carbonate and potassium carbonate. The resulting precipitate comprises a mixture of cobalt carbonate and cobalt hydroxide. The precipitate step may be represented by the following formula:

$$2Co(H_2O)_6^{+2} + 4Cl^- + 2HCl + 2NaOH + 2Na_2CO_3 \rightarrow 6NaCl + CO_2 + 13H_2O + CoCO_3 \downarrow + Co(OH)_2 \downarrow \quad (6)$$

Recoveries of cobalt exceeding 90% may be obtained by the present invention.

Thus, it is seen that in accordance with the present invention, cobalt is recovered from a chelate complex comprising N-acetyliminodiacetic acid by a process which first involves contacting the chelated substance with an aqueous solution of a strong mineral acid to separate the chelate as an ion. The resulting acidic solution is extracted with a hydrocarbon solution containing a quaternary ion forming amine which selectively removes the cobalt ions from the acidic solution into the hydrocarbon solution. Next, the cobalt values are stripped from the hydrocarbon solution with water to form complex cobalt anions having chloride counterions. Finally, the cobalt is precipitated as cobalt hydroxide and/or cobalt carbonate by adding a sufficient amount of an alkali hydroxide to the stripping water.

In order to reuse the cobalt as a catalyst in the production of N-acetyliminodiacetic acid, the cobalt precipitate may be converted to dicobaltoctacarbonyl by reacting the precipitate with carbon monoxide and hydrogen by techniques known to those skilled in the art. Good conversion is obtained at 150°–180° C. with a pressure of 1500–6000 psig ($1.03–4.13 \times 10^7$ Pa).

The invention is further illustrated by the following examples, wherein parts and percentages are given on a weight basis unless otherwise specified.

EXAMPLE 1

This example illustrates the preparation of N-acetyliminodiacetic acid by reacting acetamide and formaldehyde in the presence of dicobaltoctacarbonyl catalyst and the recovery of the cobalt catalyst from the reaction product using a hydroxamic acid toluene extractant.

Acetamide (5.91 g. 0.100 mol), paraformaldehyde (9.00 g, 0.300 mol), $H_2O$ (5.39 g, 0.299 mol), $Co_2(CO)_8$ (1.00 g., 0.00292 mol), and 1,4-dioxane (100 ml) were added to a 300 ml Hastelloy B autoclave containing a stirrer which had been flushed with argon. The stirrer was bolted onto the autoclave. The system was flushed with argon and then twice with 90:10 $CO/H_2$ mixture. The reaction vessel was pressured to 1600 psig ($1.10 \times 10^7$ Pa) with 90:10 $CO:H_2$. The mixture was heated to 100° C. The mixture was stirred at 100° C. for 2 hours. The pressure inside the reaction vessel decreased to 1308 psig ($9.0 \times 10^6$ Pa). The solution was allowed to cool to room temperature and the gas was vented from the autoclave. After flushing the autoclave with argon, the solution was removed from the autoclave. The mixture was purged with air for 1 hour at 70° C. to convert the remaining $Co^0$ to $Co^{2+}$ and then concentrated under reduced pressure to afford N-acetyliminodiacetic acid as a dark blue resin: $^1H$ NMR (acetone -$d^6$) δ 2.07 (s, 3H, $CH_3$), 4.12 (s, 2H, $CH_2$), 4.24 (s, 2H, $CH_2$), 8.17-9.03 (br s, 2H, $CO_2H$).

The resin was dissolved in 100 ml of water (pH = 1.7) and adjusted to pH 9 with aqueous $NH_4OH$. The aqueous solution was washed with a 200 ml toluene solution of N-methyldecanohydroxamic acid (3.02 g, 0.015 mol) followed by a 100 ml toluene solution of N-methyldecanohydroxamic acid (1.60 g, 0.0079 mol). The organic extracts were combined and washed with two 100 ml portions of an aqueous solution containing $NH_4OH$ and $(NH_4)_2CO_3$. The combined aqueous extracts were concentrated under reduced pressure to afford 1.13 g of a purple solid. Analysis by I.C.A.P. indicated the presence of cobalt (19.6 wt. %) and elemental analysis indicated a carbon level of 22 wt. % which suggested the presence of N-acetyliminodiacetic acid and/or iminodiacetic acid. The exact nature of the cobalt species was not determined. Although a significant amount of cobalt is recoverable by this method, a recovery of only 70% was realized. As can be seen in the subsequent example, by the practice of the present invention, cobalt recoveries in excess of 99% can be obtained.

EXAMPLE 2

This example illustrates the recovery of the cobalt catalyst values by the practice of the present invention.

The reaction described in Example 1 was repeated using 35.4 g (0.600 mol) of acetamide and 6.16 g (0.0180 mol) of $Co_2(CO)_8$ (34% Co assay=2.09 g Co). After the solution containing N-acetyliminodiacetic acid was removed from the autoclave, it was placed in a 2000 ml round bottom flask, the mixture was slowly heated to reflux over a 2-hour period, and the solution was then distilled under atmospheric pressure over a 2-hour, 45-minute period. The volatiles (1,4-dioxane, $H_2O$ were distilled into a flask containing 100 ml of 1.0 M $Na_2CO_3$ (aq).

The dark red resin (N-acetyliminodiacetic acid) was dissolved in 300 ml of concentrated hydrochoric acid. The mixture was then carefully extracted (3×300 ml) with a solution of trilauryl amine obtained under the name of Alamine 304 (225 g per 3000 ml of solution) and isodecanol (180 g per 3000 ml of solution) in a hydrocarbon obtained under the name of Kermac 270B so as not to entrain any of the aqueous layer in the organic phase. Kermac 470B chemically is a kerosene. The extractions were performed in a separatory funnel and each extraction required 5 minutes of agitation. The dark blue organic extracts were combined (2600 ml) and the solution was then stirred vigorously for 30 minutes with 260 ml of water. The phases were separated and the procedure was repeated three more times. The pink-colored aqueous layers were combined (pH~0) and titrated first to a pH of about 5 with 20 ml of 50% aqueous NaOH and then with 200 ml of 1.0 M aqueous $Na_2CO_3$ to pH of 10.5. A blue precipitate which formed during the pH adjustment was filtered and then dried in a vacuum oven. Analysis of the dark purple solid (3.853 g) by I.C.A.P. indicated the presence of 2.08 g of cobalt (99.5% recovery) and 0.8 wt. % of sodium. Analysis by I.C.A.P. of the filtrate and the distillate (1,4-dioxane/$H_2O$) indicated the presence of 6.4 mg of cobalt (0.3% recovery) and 3.1 mg of cobalt (0.1% recovery), respectively. Elemental analysis (C,H,N) of the purple solid indicated the presence of carbon (6.4%), hydrogen (2.0%), and nitrogen (<0.2%).

While the illustrated embodiments of the invention have been described with particularity, it will be understood that various other modifications will be apparent or can be readily made by those skilled in the art without departing from the spirit and scope of the invention. Accordingly, it is not intended that the scope of the claims appended hereto be limited to the examples and description as set forth hereinabove but rather that the claims be construed as encompassing all the features of patentable novelty which reside in the present invention, including all features which would be treated as equivalents thereof by those skilled in the art.

What is claimed is:

1. A process for recovering cobalt values from a mixture of N-acetyliminodiacetic acid and a cobalt catalyst used to produce the N-acetyliminodiacetic acid which comprises:
    (a) dissolving said mixture in a hydrochloric acid solution or hydrobromic acid solution;
    (b) extracting the resulting acid solution with an extractant which consists essentially of a liquid hydrocarbon solvent containing an effective cobalt extracting amount of a trialkylamine;
    (c) separating the extractant phase containing the cobalt values from the aqueous phase;
    (d) stripping the extractant phase with water;
    (e) precipitating the cobalt values from the stripping water by adding an alkali metal hydroxide or alkali metal carbonate; and
    (f) recovering the precipitated cobalt values.

2. The process of claim 1 wherein the trialkylamine has the following formula

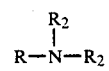

wherein R, $R_1$, and $R_2$ are independently straight or branched chain alkyl radicals having 1–20 carbon atoms.

3. The process of claim 2 wherein the alkyl radicals have about 8–16 carbon atoms.

4. The process of claim 3 wherein the trialkylamine is trilaurylamine.

5. The process of claim 1 wherein the liquid hydrocarbon solvent is kerosene or toluene.

6. The process of claim 1 wherein the liquid hydrocarbon solvent contains at least 5% by weight of the trialkylamine, based on the total weight of the extractant.

7. The process of claim 6 wherein the liquid hydrocarbon solvent contains from 5% to 50% by weight of the trialkylamine, based on the total weight of the extractant.

8. The process of claim 7 wherein the liquid hydrocarbon solvent contains from about 8% to about 40% by weight of the trialkylamine based on the total weight of the extractant.

9. The process of claim 1 wherein an alkali metal hydroxide is added to precipitate the cobalt values.

10. The process of claim 9 wherein the alkali metal hydroxide is sodium hydroxide.

11. The process of claim 1 wherein the mixture is dissolved in a hydrochloric acid solution.

12. A process for recovering cobalt values from a mixture of N-acetyliminodiacetic acid and a cobalt catalyst used to produce the N-acetyliminodiacetic acid which comprises:
    (a) dissolving the mixture in a hydrochloric acid solution;
    (b) extracting the resulting acid solution with an extractant which consists essentially of kerosene or toluene containing at least 5% by weight of trilaurylamine, based on the total weight of the extractant;

(c) separating the extractant phase containing the cobalt values from the aqueous phase;

(d) stripping the extractant phase with water;
(e) precipitating the cobalt values from the stripping water by adding an alkali metal hydroxide; and
(f) recovering the precipitated cobalt values.

* * * * *